(12) United States Patent
Fu et al.

(10) Patent No.: US 12,118,739 B2
(45) Date of Patent: Oct. 15, 2024

(54) MEDICAL IMAGE PROCESSING METHOD, APPARATUS, AND DEVICE, MEDIUM, AND ENDOSCOPE

(71) Applicant: TENCENT TECHNOLOGY (SHENZHEN) COMPANY LIMITED, Shenzhen (CN)

(72) Inventors: Xinghui Fu, Shenzhen (CN); Han Zheng, Shenzhen (CN); Junwen Qiu, Shenzhen (CN); Hong Shang, Shenzhen (CN); Zhongqian Sun, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 411 days.

(21) Appl. No.: 17/520,715

(22) Filed: Nov. 7, 2021

(65) Prior Publication Data
US 2022/0058821 A1    Feb. 24, 2022

Related U.S. Application Data

(63) Continuation of application No. PCT/CN2020/125764, filed on Nov. 2, 2020.

(30) Foreign Application Priority Data

Nov. 25, 2019    (CN) .......................... 201911168526.X

(51) Int. Cl.
*G06T 7/60*    (2017.01)
*A61B 1/31*    (2006.01)
(Continued)

(52) U.S. Cl.
CPC ................ *G06T 7/60* (2013.01); *G06F 18/24* (2023.01); *G06T 7/0014* (2013.01); *G06T 7/73* (2017.01);
(Continued)

(58) Field of Classification Search
CPC . G06F 18/213; G06F 18/24; A61B 1/000094; A61B 1/000096; A61B 1/31;
(Continued)

(56) References Cited

U.S. PATENT DOCUMENTS 5,967,968 A     10/1999 Nishioka
10,231,600 B2 *  3/2019 Ikemoto ............... A61B 5/0084
(Continued)

FOREIGN PATENT DOCUMENTS

| CN | 103505217 A | 1/2014 |
| CN | 103505218 A | 1/2014 |

(Continued)

OTHER PUBLICATIONS

Lequan Yu et al., "Integrating Online and Offline Three-Dimensional Deep Learning for Automated Polyp Detection in Colonoscopy Videos, " Jan. 31, 2017, IEEE Journal of Biomedical and Health Informatics, vol. 21, No. 1, Jan. 2017, pp. 66-73.*
(Continued)

*Primary Examiner* — Omar S Ismail
(74) *Attorney, Agent, or Firm* — ANOVA LAW GROUP, PLLC

(57) ABSTRACT

A medical image processing method includes: determining a target mask of a target object in a medical image and a reference mask of a reference object in the medical image, the target mask indicating a position and a boundary of the target object, and the reference mask indicating a position and a boundary of the reference object; determining a feature size of the target object based on the target mask; determining a feature size of the reference object based on the reference mask; and determining a target size of the target object based on the feature size of the reference object,
(Continued)

a preset mapping relationship between the feature size of the reference object and a reference size, and the feature size of the target object.

20 Claims, 5 Drawing Sheets

(51) Int. Cl.
*G06F 18/24* (2023.01)
*G06T 7/00* (2017.01)
*G06T 7/73* (2017.01)

(52) U.S. Cl.
CPC ....... *A61B 1/31* (2013.01); *G06T 2207/10016* (2013.01); *G06T 2207/10068* (2013.01); *G06T 2207/20081* (2013.01); *G06T 2207/20084* (2013.01); *G06T 2207/30004* (2013.01); *G06V 2201/03* (2022.01)

(58) Field of Classification Search
CPC . G06T 2207/10016; G06T 2207/10068; G06T 2207/20081; G06T 2207/20084; G06T 2207/30004; G06T 2207/30032; G06T 2207/30096; G06T 7/0014; G06T 7/60; G06T 7/73; G06V 10/25; G06V 10/75; G06V 10/82; G06V 2201/03; G06V 2201/031
See application file for complete search history.

(56) References Cited

U.S. PATENT DOCUMENTS

| | | | |
|---|---|---|---|
| 2012/0106809 A1* | 5/2012 | Lee | G06V 10/267 382/128 |
| 2013/0023715 A1 | 1/2013 | Raleigh et al. | |
| 2014/0307930 A1* | 10/2014 | Lee | G06V 20/695 382/128 |
| 2016/0300343 A1* | 10/2016 | Gazit | G06T 7/0014 |
| 2017/0112353 A1* | 4/2017 | Ikemoto | A61B 1/0002 |
| 2018/0253839 A1* | 9/2018 | Zur | A61B 1/000094 |
| 2019/0206053 A1* | 7/2019 | Ichiki | G06T 7/0012 |
| 2019/0320875 A1* | 10/2019 | Jones | G06T 7/0012 |
| 2020/0285876 A1* | 9/2020 | Usuda | A61B 1/000094 |
| 2021/0327563 A1* | 10/2021 | He | G06V 10/462 |
| 2022/0012874 A1* | 1/2022 | Maier-Hein | G06T 7/254 |
| 2022/0012890 A1* | 1/2022 | Wu | G06T 7/0012 |
| 2022/0020496 A1* | 1/2022 | Saito | G06T 7/0012 |

FOREIGN PATENT DOCUMENTS

| | | |
|---|---|---|
| CN | 104240264 A | 12/2014 |
| CN | 107507188 A | 12/2017 |
| CN | 109141250 A | 1/2019 |
| CN | 111091536 A | 5/2020 |
| WO | WO-2005023086 A2 * 3/2005 ........... G06T 7/0014 |

OTHER PUBLICATIONS

Ahmed Mohammed, "Y-Net: A deep Convolutional Neural Network for Polyp Detection, "Jun. 5, 2018, Computer Vision and Pattern Recognition, British Machine Vision Conference (BMVC), 2018, pp. 1-7.*
Ronald M. Summers, "Polyp Size Measurement at CT Colonography: What Do We Know and What Do We Need to Know?, "Oct. 15, 2010, Radiology: vol. 255, No. 3—Jun. 2010, pp. 707-711.*
Ngoc-Quang Nguyen, "Robust Boundary Segmentation in Medical Images Using a Consecutive Deep Encoder-Decoder Network," Mar. 29, 2019, IEEEAccess, vol. 7,2019, pp. 33795-33805.*
Mazin Abed Mohammed, "A real time computer aided object detection of nasopharyngeal carcinoma using genetic algorithm and artificial neural network based on Haar feature fear," Jul. 18, 2018, Future Generation Computer Systems 89 (2018), pp. 539-545.*
Kaiming He et al., "Mask R-CNN," Oct. 2017, Proceedings of the IEEE International Conference on Computer Vision (ICCV) 2017, pp. 2961-2968.*
European Patent Office European Search Report for Application No. 20892052.0 Aug. 1, 2022 8 pages.
The World Intellectual Property Organization (WIPO) International Search Report for PCT/CN2020/125764 Feb. 4, 2021 7 Pages (including translation).
Kaiming He et al., "Mask R-CNN," Proceedings of the IEEE International Conference on Computer Vision (ICCV), 2017, pp. 2961-2969. 9 pages.
R.M. Summers, "Polyp Size Measurement at CT Colonography: What Do We Know and What Do We Need to Know?," Radiology, 2010. 14 pages.

* cited by examiner

MEDICAL IMAGE PROCESSING METHOD, APPARATUS, AND DEVICE, MEDIUM, AND ENDOSCOPE

CROSS-REFERENCES TO RELATED APPLICATIONS

This application is a continuation application of PCT Patent Application No. PCT/CN2020/125764, filed on Nov. 2, 2020, which claims priority to Chinese Patent Application No. 201911168526.X, entitled "MEDICAL IMAGE PROCESSING METHOD, APPARATUS, AND DEVICE, MEDIUM, AND ENDOSCOPE" filed with the National Intellectual Property Administration, PRC on Nov. 25, 2019, the entire contents of both of which are incorporated herein by reference.

FIELD OF THE TECHNOLOGY

The present disclosure relates to the field of image processing, and more specifically, to a medical image processing method, apparatus, and device, a medium, and an endoscope.

BACKGROUND OF THE DISCLOSURE

In a process of performing medical examinations and operations by using medical electronic devices, medical images acquired by using the medical electronic devices need to be processed to help users learn more information. The users can observe a state of a biological tissue of an examined object in real time by using the medical electronic devices such as an endoscope. For example, the endoscope can be put into a body cavity, such as a digestive tract, an intestinal tract, a trachea, or another cavity of the examined object for observation.

SUMMARY

An embodiment of the present disclosure provides a medical image processing method, including: determining a target mask of a target object in a medical image and a reference mask of a reference object in the medical image, the target mask indicating a position and a boundary of the target object, and the reference mask indicating a position and a boundary of the reference object; determining a feature size of the target object based on the target mask; determining a feature size of the reference object based on the reference mask; and determining a target size of the target object based on the feature size of the reference object, a preset mapping relationship between the feature size of the reference object and a reference size, and the feature size of the target object.

An embodiment of the present disclosure further provides a medical image processing apparatus, including: a target detection unit, configured to determine a target mask of a target object in a medical image and a reference mask of a reference object in the medical image, the target mask indicating a position and a boundary of the target object, and the reference mask indicating a position and a boundary of the reference object; a feature size determining unit, configured to: determine a feature size of the target object based on the target mask; and determine a feature size of the reference object based on the reference mask; and a target size determining unit, configured to determine a target size of the target object based on the feature size of the reference object, a preset mapping relationship between the feature size of the reference object and a reference size, and the feature size of the target object.

An embodiment of the present disclosure further provides an endoscope, including: an image acquisition unit, configured to acquire a medical image; a processing unit, configured to perform the foregoing method to determine a target size of a target object in the medical image; and an output unit, configured to output the target size of the target object.

An embodiment of the present disclosure further provides a medical image processing device, including: one or more processors; one or more memories, the memory storing computer-readable code, the computer-readable code, when executed by the one or more processors, performing: determining a target mask of a target object in a medical image and a reference mask of a reference object in the medical image, the target mask indicating a position and a boundary of the target object, and the reference mask indicating a position and a boundary of the reference object; determining a feature size of the target object based on the target mask; determining a feature size of the reference object based on the reference mask; and determining a target size of the target object based on the feature size of the reference object, a preset mapping relationship between the feature size of the reference object and a reference size, and the feature size of the target object.

An embodiment of the present disclosure further provides a non-transitory computer-readable storage medium, storing instructions, the instructions, when executed by a processor, causing the processor to perform the foregoing method.

Through a medical image processing method, apparatus, and device, a medium, and an endoscope provided in the present disclosure, a target object in a medical image may be processed in real time to determine an actual size of the target object, so as to provide users with size information of the target object in real time.

BRIEF DESCRIPTION OF THE DRAWINGS

To describe the technical solutions of the embodiments of the present disclosure more clearly, the following briefly introduces the accompanying drawings required for describing the embodiments. Apparently, the accompanying drawings in the following description show only some embodiments of the present disclosure, and a person of ordinary skill in the art may still derive other drawings from these accompanying drawings without creative efforts. The following accompanying drawings are not deliberately scaled to an actual size, but are intended to show the purpose of the present disclosure.

DESCRIPTION OF EMBODIMENTS

Figure 1:
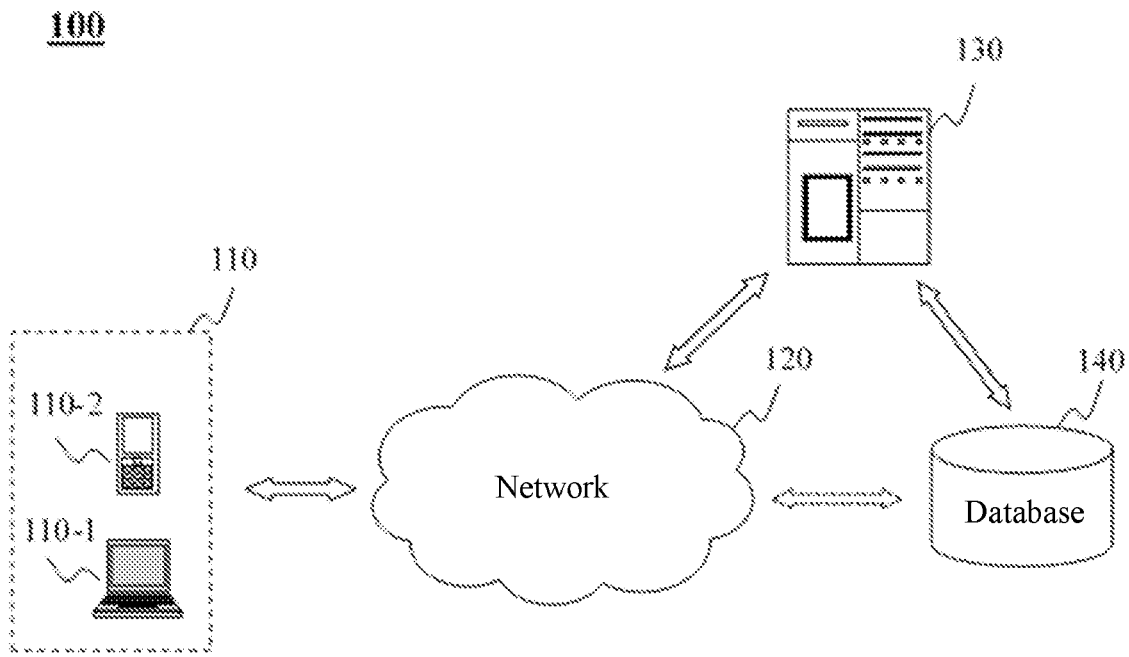
FIG. 1 is an exemplary scenario diagram of an image processing system for implementing medical image processing according to the present disclosure.

The technical solutions in embodiments of the present disclosure are clearly and completely described in the following with reference to the accompanying drawings. Apparently, the described embodiments are merely some rather than all of the embodiments of the present disclosure. All other embodiments obtained by a person of ordinary skill in the art based on the embodiments of the present disclosure without creative efforts shall fall within the protection scope of the present disclosure.

As shown in the present disclosure and the claims, words such as "a/an", "one", "one kind", and/or "the" do not refer specifically to singular forms and may also include plural forms, unless the context expressly indicates an exception. In general, terms "comprise" and "include" merely indicate including clearly identified steps and elements. The steps and elements do not constitute an exclusive list. A method or a device may also include other steps or elements.

Although the present disclosure makes various references to some modules in the system according to the embodiments of the present disclosure, any quantity of different modules may be used and run on a user terminal and/or a server. The modules are only illustrative, and different aspects of the system and method may use different modules.

Flowcharts are used in the present disclosure for illustrating operations performed by the system according to the embodiments of the present disclosure. It is to be understood that, the foregoing or following operations are not necessarily strictly performed according to an order. On the contrary, the operations may be performed in a reverse order or simultaneously as required. Meanwhile, other operations may be added to the processes. Alternatively, one or more operations may be deleted from the processes.

A (computer vision) CV is a science that studies how to use a machine to "see", and furthermore, that uses a camera and a computer to replace human eyes to perform machine vision such as recognition, tracking, and measurement on a target, and further perform graphic processing, so that the computer processes the target into an image more suitable for human eyes to observe, or an image transmitted to an instrument for detection. As a scientific discipline, CV studies related theories and technologies and attempts to establish an AI system that can obtain information from images or multidimensional data. The CV technology usually includes technologies such as image processing, image recognition, image semantic understanding, image retrieval, optical character recognition (OCR), video processing, video semantic understanding, video content/behavior recognition, three-dimensional (3D) object reconstruction, 3D technology, virtual reality (VR), augmented realty (AR), simultaneous localization, and map construction, and further includes biometric identification technologies such as face recognition and finger recognition.

The technical solutions of the embodiments of the present disclosure relate to processing a medical image by using the CV technology in an artificial intelligence (AI) technology.

Sometimes, a size of an observed target object needs to be measured when a to-be-examined object is examined by using a medical electronic device. For example, during a colon examination by using an electronic endoscope, a size of a polyp is a key indicator of an examination result. According to statistics, two polyps of sizes of 6 mm and 10 mm are of important clinical value.

In some methods, a target object (for example, a polyp) in an image is measured manually. Manually-measured data may be affected by deformation of lens or changes in the nature of a biological tissue during operation.

In view of this, the present disclosure provides a new medical image processing method, which can rapidly provide users with a measure result (refer to as a target size in the following) of an actual size of a target object in an image in real time.

FIG. 1 is an exemplary scenario diagram of an image processing system for implementing medical image processing according to the present disclosure. As shown in FIG. 1, the image processing system 100 may include a user terminal 110, a network 120, a server 130, and a database 140.

The user terminal 110 may be a computer 110-1 or a mobile phone 110-2 shown in FIG. 1. It may be understood that, actually, the user terminal may be any another type of electronic device being capable of processing data, and may include, but not limited to: a desktop computer, a notebook computer, a tablet computer, a smartphone, a smart home device, a wearable device, an in-vehicle electronic device, a surveillance device, a medical electronic device, and the like.

The user terminal provided in the present disclosure may be configured to receive an image, and process the image by using the method provided in the present disclosure. For example, the user terminal may acquire an image by using an image acquisition device (for example, a camera and a video camera) arranged on the user terminal. In another example, the user terminal may alternatively receive an image from an image acquisition device disposed independently. In still another example, the user terminal may alternatively receive an image from a server through a network. The image may be an individual image, or may be a frame in a video. When the image is a medical image, the user terminal may alternatively be connected to a medical electrical device, and receive the image from a medical electrical device. The medical image may be a medical image acquired by using computerized tomography (CT), magnetic resonance imaging (MRI), ultrasound, X-ray, radionuclide imaging (such as SPECT and PET), and other methods, or may be an image displaying human physiological information by using an electrocardiogram, an electroencephalogram, optical photography, an endoscope image, and the like.

The image processing method provided in the present disclosure may be performed by one or more computing devices, for example, the user terminal 110 and/or the server 130.

In some embodiments, the image processing method provided in the present disclosure may be performed by using a processing unit of the user terminal. In some embodiments, the user terminal may perform the image processing method by using an application arranged inside the user terminal. In some other implementations, the user terminal may perform the image processing method provided in the present disclosure by calling an external stored application of the user terminal.

In some other embodiments, the user terminal transmits the received image to the server 130 by using the network 120, so that the server 130 performs the image processing method. In some embodiments, the server 130 may perform the image processing method by using an application arranged inside the server. In some other implementations, the server 130 may perform the image processing method by calling an external stored application of the server.

In still some embodiments, after performing a part of the image processing method on the received image, the user terminal transmits image data obtained after the processing to the server 130 by using the network 120, so that the server 130 performs the other part of the image processing method. That is, the image processing method may be completed by the user terminal and the server collaboratively.

The network 120 may be an individual network, or a combination of at least two different networks. For example, the network 120 may include, but not limited to one of or a combination of some of a local area network, a wide area network, a common network, a private network, and the like.

The server 130 may be an individual server, or a server cluster, and servers in the group are connected by using a wired or wireless network. A server cluster may be centralized, such as a data center, or may be distributed. The server 130 may be local or remote.

The database 140 may generally be referred to as a device having a storage function. The database 140 is mainly configured to store various data used, produced, and outputted by the user terminal 110 and the server 130 during operation. The database 140 may be local or remote. The database 140 may include various memories, for example, a random access memory (RAM) and a read only memory (ROM). Storage devices mentioned above are only some examples, and storage devices that may be used by the system are not limited thereto.

The database 140 may be connected to or in communication with a part or all of the server 130 by using the network 120, or directly connected to or in communication with the server 130, or in a manner of a combination of the foregoing two manners.

In some embodiments, the database 140 may be an independent device. In some other embodiments, the database 140 may alternatively be integrated in at least one of the user terminal 110 and the server 130. For example, the database 140 may be disposed on the user terminal 110, or may be disposed on the server 130. In another example, the database 140 may alternatively be distributed, a part of the database being disposed on the user terminal 110, and the other part of the database being disposed on the server 130.

Figure 2:
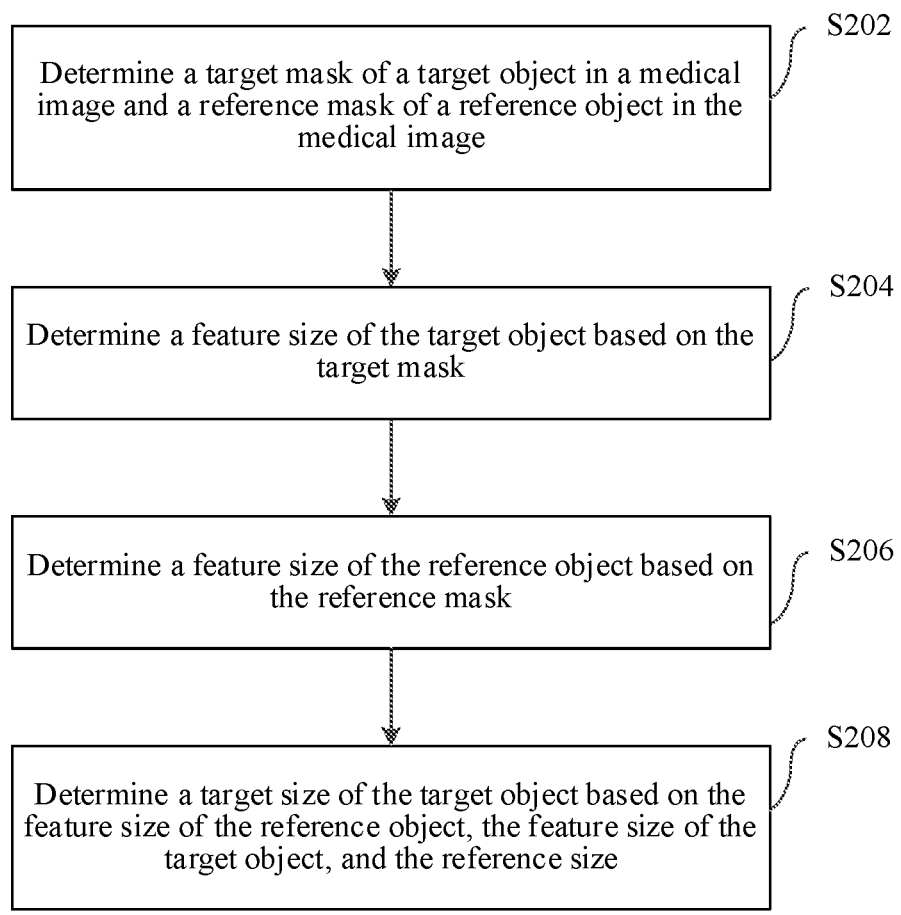
FIG. 2 is a schematic flowchart of a medical image processing method according to an embodiment of the present disclosure.

FIG. 2 is a schematic flowchart of a medical image processing method according to an embodiment of the present disclosure. The method may be performed by one or more computing devices, for example, the user terminal 110 and/or the server 130.

In step S202, target detection may be performed on a medical image to determine a target object and a reference object in the medical image. The target object may be a tissue object that a user intends to observe in a medical image, for example, a cancer tissue, a polyp, anabrosis, erosion, edema, or another object. The reference object may be an object with a known reference size, for example, a medical instrument used during operating by using a medical electronic device, such as a scalpel, an electric scalpel, a suturing device, a pair of tweezers, or a pair of biopsy forceps, or a part of a medical instrument, such as a head of a pair of biopsy forceps and a part of a ring body of a polyp ring.

In some embodiments, in a medical image acquired during an intestinal examination by using an endoscope, a target image may be an image of a polyp, and a reference image may be an image of a head of a pair of biopsy forceps. It may be understood that, during acquiring by using other types of medical electronic devices, the target object and the reference object involved in the present disclosure may be any other objects.

In some embodiments, the reference size may be a maximum size of an instrument. For example, when the reference object is a head of a pair of biopsy forceps, the reference size may be a size of the head of the pair of biopsy forceps, such as a length, a width, or the like. When the reference object is a part of a ring body of a polyp ring, the reference size may be a size of the polyp ring, for example, a radius of the polyp ring, a thickness of the ring body, or the like.

In some embodiments, the target detection may be performed by processing the medical image by using a neural network. For example, the medical image may be processed by using networks such as an RCNN (region-based convolutional neural network), a fast RCNN, a faster RCNN, a YOLO (You Only Look Once), an SSD (single-shot detector), a Mask RCNN, a deepLab, and other series, to recognize a target object and a reference object in the medical image. The Mask RCNN is used as an example to describe the principle of the present disclosure in the following. In other embodiments, the target detection may be performed by using any other forms of neural networks or variations of the neural networks.

Figure 3:
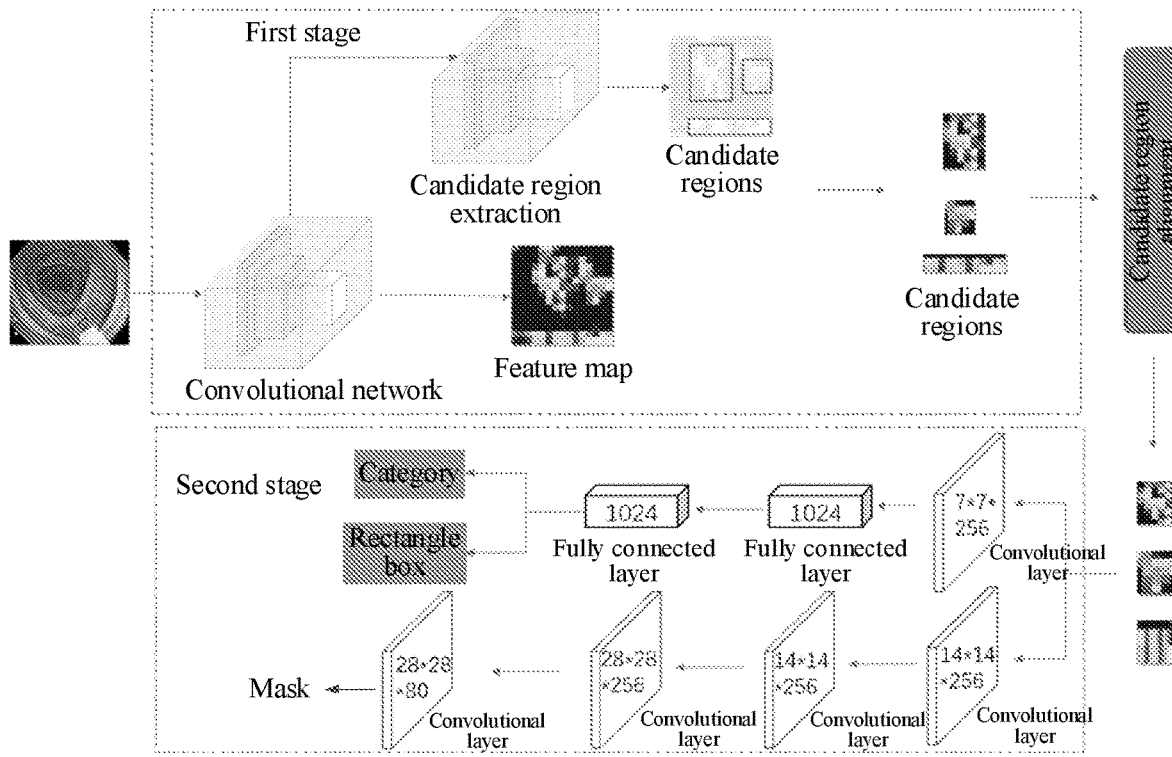
FIG. 3 shows a network architecture of a Mask region-based convolutional neural network (RCNN).

FIG. 3 shows a network architecture of a Mask RCNN. As shown in FIG. 3, the Mask RCNN adopts an idea of detecting the network faster RCNN by using two stages. The first stage of the Mask RCNN adopts a Resnet_FPN (Feature Pyramid Network) architecture, and is used for extracting features of candidate regions. The second stage of the Mask RCNN includes two branches. The first branch is used for predicting a target category and coordinates of a target rectangle box, and the second branch is used for predicting a target mask.

As shown in FIG. 3, during the first stage, an inputted medical image (or any other images) may be processed by using a convolutional network to obtain image features of the image.

Figure 4:
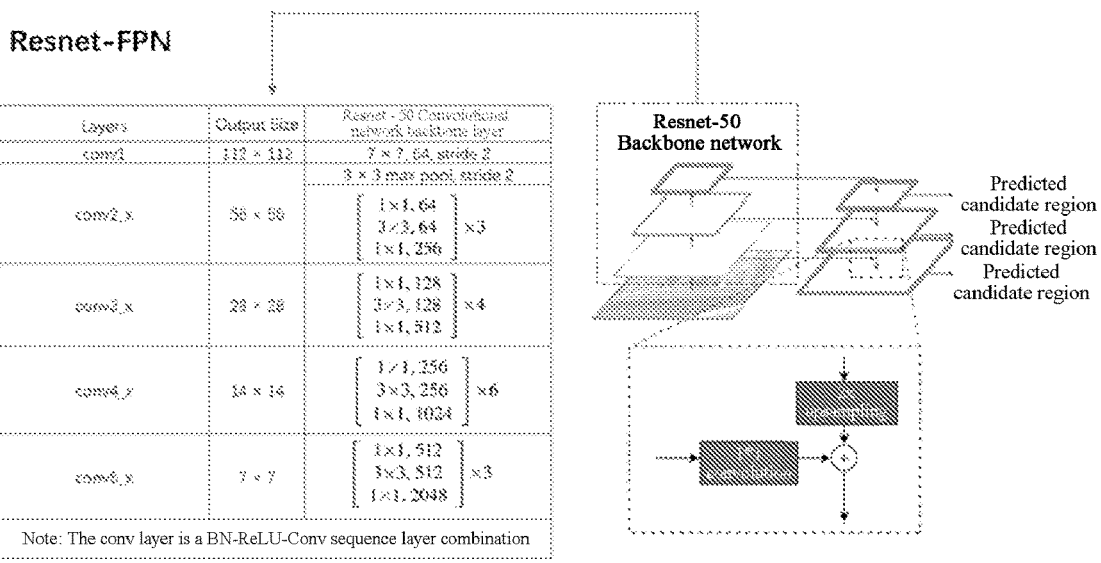
FIG. 4 is an architecture diagram of a network structure for extracting an image feature.

FIG. 4 is an architecture diagram of a network structure for extracting image features.

In some embodiments, the image features may be extracted by using a Resnet-50 network as a backbone network. In other embodiments, the image features may alternatively be extracted by using networks such as a Resnet-18, a Resnet-34, and a Resnet-101.

An example in which the Resnet-50 shown in FIG. 4 is a backbone network is used, results outputted by a conv2_$x$ layer, a conv3_$x$ layer, a conv4_$x$ layer, and a conv5_$x$ layer in the Resnet-50 network may be used as image features of the input image, and the results outputted by the four layers of the convolutional network are combined through adding. As shown in FIG. 4, the results outputted by the four layers are image features having different sizes respectively. Normalization of sizes may be performed on the four image features of different sizes by using a convolution kernel of 1*1 and an upsampling operation, and different image features obtained after the normalization may be added to combine the image features of different scales.

Candidate regions may be predicted based on a combination result combining the image features of different scales. In some embodiments, the combination result may be processed by using one or more of a sliding window, a select search, an edgebox algorithm, and a region proposal network (RPN), to obtain a detection result of the candidate regions.

Go back to FIG. 3, a plurality of candidate regions in an input image can be determined according to the input image by using the Resnet-FPN network architecture shown in FIG. 4, and subsequently, the plurality of candidate regions are used as ROIs. As shown in FIG. 3, a plurality of ROIs may have different sizes. For ease of subsequent processing, an alignment operation (e.g., image registration operation) may be performed on the plurality of ROIs of different sizes to obtain ROIs having the same size obtained after the normalization.

Figure 5:
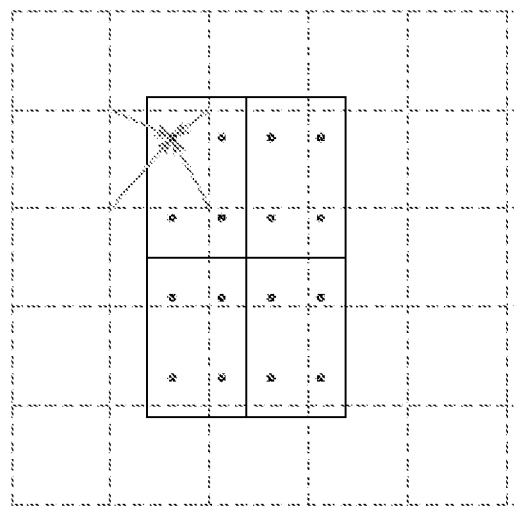
FIG. 5 is a schematic diagram of an alignment operation performed on a region of interest (ROI).

FIG. 5 is a schematic diagram of an alignment operation performed on an ROI. In some embodiments, the ROIs may be aligned in an interpolation manner. For example, a bilinear interpolation may be performed on coordinates of a floating-point number of a sampled point on a feature map corresponding to the ROIs and a feature value corresponding to the point, to obtain a value of a coordinates point in the ROIs after the alignment.

As shown in FIG. 5, a dotted line table in FIG. 5 represents a feature map, solid lines represent the ROIs determined in the process shown in FIG. 4, and solid points represent coordinates points sampled in the ROIs. A value of each coordinates point is obtained by performing a bilinear interpolation on values of adjacent dotted line cross points on the corresponding feature map. In view of this, sizes of the ROIs determined in FIG. 4 may be adjusted, and a size of an ROI of 2*2 is adjusted as 4*4.

Go back to FIG. 3, after determining the plurality of ROIs having the same size by using the process shown in FIG. 5, the ROIs having the same size may be processed by using the network structure of the second structure shown in FIG. 3.

As shown in FIG. 3, the network structure of the second stage includes two branches. The first branch is used for determining a target category and coordinates and a size of a target rectangle box in an input image.

In some embodiments, the first branch may predict the target category and the coordinates of the target rectangle box in the input image by using one convolutional network (for example, a convolutional network of 7*7*256 shown in FIG. 3 and a convolutional network of any another form) and two fully connected layers (in an example shown in FIG. 3, a fully connected layer has 1024 nerve cells). In this embodiment of the present disclosure, a target type detected in the process shown in FIG. 3 may include a target of a biological tissue type and a target of a non-biological tissue type. The target of the biological tissue type may be considered as a target object involved in this embodiment of the present disclosure, and the target of the non-biological tissue type may be considered as a reference object involved in this embodiment of the present disclosure.

In some embodiments, the target of the biological tissue type may include a cancer tissue, a polyp, anabrosis, erosion, edema, and the like. The target of the non-biological tissue type may include a scalpel, an electric scalpel, a suturing device, a pair of tweezers, and a pair of biopsy forceps.

The second branch may be used for determining a mask of a target detected in an input image. As shown in FIG. 3, the mask of the target may be determined by using 4 convolution layers. In the example shown in FIG. 3, sizes of the four convolution layers are respectively 14*14*256, 14*14*256, 28*28*256, and 28*28*80. It may be understood that, the network structure shown in FIG. 3 does not constitute a limitation to the present disclosure. A person skilled in the art may arrange parameters and structures of convolution layer in the network structure according to an actual situation.

A target mask of the target object and a reference mask of the reference object can be determined in the manner shown in FIG. 3. The target mask indicates a position of the target object and a boundary of the target object, and the reference mask indicates a position of the reference object and a boundary of the reference object.

In some embodiments, the target mask and the reference mask may be a binary image composed of 0 and 1, and a region of value 1 may correspond to a target object and a reference object detected in an input image. It may be understood that, the position and boundary of the target object and the position and boundary of the reference object can be determined by using a position and boundary of the region of value 1.

It may be understood that, because the reference object is a non-biological tissue such as a scalpel, an electric scalpel, a suturing device, a pair of tweezers, and a pair of biopsy forceps, and therefore, these reference objects usually have known shapes and sizes. Because the position and boundary of the target object and the position and boundary of the reference object can be segmented from the input image separately by using the method shown in FIG. 3, a size of the target object may be determined by using the shapes and sizes of the known reference object.

In step S204, a feature size of the target object may be determined based on the target mask.

The feature size may refer to information related to a size of an object in a medical image. In some embodiments, the feature size of the target object may include a plurality of feature sizes. For example, the plurality of feature sizes may include a distance between two most distant points in the target object, and distances between the two most distant points and a center point of the medical image.

Step S204 may include: determining two target feature points in the target mask, a distance between the two target feature points indicating a maximum size of the target mask. The distance between the two target feature points may be determined as a first feature size of the target object.

Further, step S204 may further include: determining a distance between one target feature point in the two target feature points and a center of the medical image as a second feature size of the target object; and determining a distance between the other target feature point in the two target feature points and the center of the medical image as a third feature size of the target object.

In step S206, a feature size of the reference object may be determined based on the reference mask.

In some embodiments, the feature size of the reference object and the feature size of the target object are determined in the same manner.

In some embodiments, the feature size of the reference object may include a plurality of feature sizes. The plurality of feature sizes may include a distance between two most distant points in the reference object, and distances between the two most distant points and a center point of the medical image.

For example, step S206 may include: determining two reference feature points in the reference mask, a distance between the two reference feature points indicating a maximum size of the reference mask; and determining the distance between the two reference feature points as a first feature size.

Further, step S206 may further include: determining a distance between one reference feature point in the two reference feature points and a center of the medical image as a second feature size; and determining a distance between the other reference feature point in the two reference feature points and the center of the medical image as a third feature size of the reference object.

In step S208, a target size of the target object may be determined based on the feature size of the reference object, the feature size of the target object, and the reference size, the reference size and the feature size of the reference object having a predefined mapping relationship. That is, a target size of the target object is determined based on the feature size of the reference object, a preset mapping relationship between the feature size of the reference object and a reference size, and the feature size of the target object.

In some embodiments, Step S208 may include: determining at least one mapping parameter used in the mapping relationship based on the reference size and the feature size of the reference object. In some embodiments, the at least one mapping parameter is determined by using the following steps: fitting the feature size of the reference mask determined by using at least one related medical image, to determine the at least one mapping parameter. The at least one related medical image may be frame(s) of images in a same medical video stream as the medical image currently being processed.

In some embodiments, the mapping relationship may be represented as that: the reference size can be represented as a function f of the feature size of the reference object. That is:

$$L = f(x, y, z, \ldots) \tag{1}$$

where L represents the reference size of the reference object, and x, y, and z represent three a feature size of the reference object. Although an example in which the reference object includes three types of feature sizes is used in the present disclosure to describe the principle of the present disclosure, a person skilled in the art may understand that, when the reference object includes more or less types of feature sizes determined in other manners, the mapping relationship represented by using the formula (1) may be expanded correspondingly.

In some embodiments, f may be represented in a form of a polynomial. The polynomial includes at least one variable, the at least one variable represents the feature size of the reference object, and the mapping parameter is a coefficient of each term in the polynomial. For example, the mapping relationship may be represented by using the formula (2):

$$L = \Sigma^{a,b,c} k_{abc} {}^* x^a {}^* y^b {}^* z^c \tag{2}$$

where a, b, and c are integers with values in a range of [0, 1], L is the reference size of the reference object, and x, y, and z represent the first feature size, the second feature size, and the third feature size of the reference object respectively. $K_{abc}$ represents the mapping parameter. The foregoing formula (2) may be equivalent to the formula (3):

$$L = k_0 + k_1 {}^* x + k_2 {}^* y + k_3 {}^* z + k_4 {}^* xy + k_5 {}^* xz + k_6 {}^* yz + k_7 {}^* xyz \tag{3}$$

That is, the reference size of the reference object may be represented as a polynomial formed by using the feature size of the reference object as variables.

When the mapping relationship is represented as the foregoing formula (2) (that is, the formula (3)), because the mapping relationship includes 8 mapping parameters, the feature size of the reference object determined based on eight medical images and the reference size of the known reference object may be fitted, to determine the foregoing mapping parameters $k_0$ to $k_7$.

In some other implementations, the foregoing mapping relationship f may alternatively be represented as a functional expression of any another form. For example, the mapping relationship f may be represented by using a power function, an exponential function, a trigonometric function, and a function of any another form, and correspondingly, at least one mapping parameter in the mapping relationship may be determined.

A feature size of the target size may be processed by using the determined mapping parameter based on the mapping relationship, to determine the target size of the target object. For example, the target size of the target object is determined according to the feature size of the target object and the at least one mapping parameter.

That is, after determining a value of the mapping parameter in the formula (2) by using the foregoing method, the target size of the target object may be determined by using the formula (4):

$$D = \Sigma^{a,b,c} k_{abc} {}^* x_o^a {}^* y_o^b {}^* z_o^c \tag{4}$$

where D represents the target size of the target object, $k_{abc}$ is the mapping parameter determined by using the foregoing method, and $x_o$, $y_o$, and $z_o$ represent the first feature size of the target object, the second feature size of the target object, and the third feature size of the target object respectively.

After determining the mapping parameter by using the foregoing method, for any medical image, a target size of a target object in the medical image may be determined by using the formula (4).

In some embodiments, for any medical image, a target size of a target object in the medical image may be determined based on a medical image set, including a plurality of medical images, of the medical image.

For example, candidate target sizes of a target object in each medical image in the medical image set may be determined by using the formula (4), and a target size of the target object in the medical image may be determined by using the formula (5).

$$P_{size} = \Sigma_i \{D\}_i / n \tag{5}$$

where n represents a quantity of a plurality of medical images included in a medical image set, i is an index parameter, and $\{D\}_i$ is a candidate target size of a target object determined by using an $i^{th}$ medical image.

That is, the target size of the target object may be determined based on an average value of candidate target sizes of the target object determined by using the plurality of medical images. In some other implementations, the target size of the target object may alternatively be determined by using a weighted average of the candidate target sizes of the target object determined by using a plurality of medical images. In some examples, n may be an integer greater than 10.

In some embodiments, before step S204 is performed, whether the medical image meets a preset condition may be determined according to the target mask and the reference mask determined according to step S202. When the medical image meets the preset condition, step S204 to step S208 may continue to be performed. When the medical image does not meet the preset condition, a size of the target object may not be determined based on the medical image.

For example, a frame of image may be obtained from a real-time medical video stream as the medical image, and then whether the medical image meets the preset condition is determined. When the medical image does not meet the preset condition, another frame of image is obtained from the real-time medical video stream as the medical image for the foregoing determining, until an extracted medical image meets the foregoing preset condition, and a size of a target object is determined from the medical image meeting the preset condition.

In some embodiments, the target mask and the reference mask need to meet the following conditions:

There is a target object (for example, a polyp) of a predefined type and a reference object (for example, a head of a pair of biopsy forceps) of a predefined type in a medical image.

The target mask and the reference mask are not overlapped.

A distance between the target mask and a boundary of the medical image and a distance between the reference mask and the boundary of the medical image are greater than a preset first threshold (for example, 20 pixels).

A distance between a center point of the target mask and a center point of the medical image and a distance between a center point of the reference mask and the center point of the medical image are less than a preset second threshold (for example, 50 pixels).

When the target mask and the reference mask determined in the medical image meet the foregoing conditions, it may be considered that the medical image meet a condition for determining the size of the target object, the medical image includes the complete target object and reference object, and the target object and the reference object are relatively close to the center of the image, and therefore, the deformation is relatively small.

It may be understood that, in specific applications, a person skilled in the art may adjust the foregoing conditions according to an actual situation. For example, specific values of the first threshold and second threshold may be set according to an actual situation. In addition, a person skilled in the art may alternatively select to delete at least one of the foregoing four conditions, or add a new condition according to an actual situation.

The foregoing medical image processing method may be applied to a video frame in a video stream. For example, when an inputted medical image is a video frame, a mapping parameter in the mapping relationship may be determined by using a reference mask of a reference object in a plurality of video frames (for example, 8) received previously, and a target size of a target object in a current video frame is determined by using the determined mapping parameter.

In some embodiments, mapping parameters in the mapping relationship may be updated by using a feature size of the reference object before determining the target size of the target object in the medical image each time.

In some other embodiments, the target size of the target object in the current video frame may be determined by using a result of the predetermined mapping parameter.

Through the medical image processing method provided in the present disclosure, a size of a target object in a medical image can be determined according to a result of target detection performed on the medical image, so as to make measuring a target in a medical image in real time possible. An actual size of the target object is determined by fitting a reference mask having a known reference size and an actual size in the image, and the method provided in the present disclosure has stronger robustness and effectively avoids a problem of inaccurate measurement caused by the deformation caused by the lens of the image acquisition unit.

Figure 6:
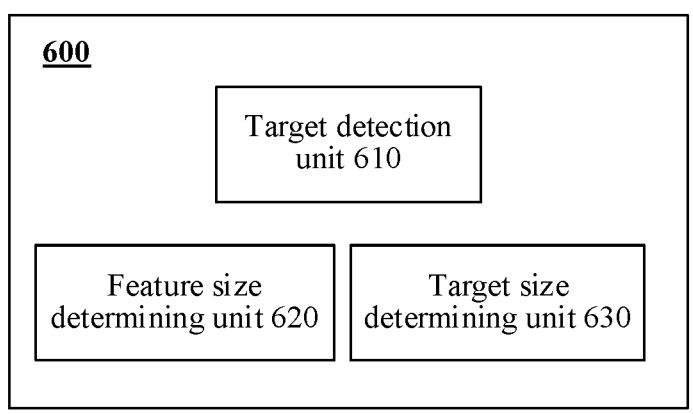
FIG. 6 is a schematic block diagram of a medical image processing apparatus according to an embodiment of the present disclosure.

FIG. 6 is a schematic block diagram of a medical image processing apparatus according to an embodiment of the present disclosure. As shown in FIG. 6, a medical image processing apparatus 600 may include a target detection unit 610, a feature size determining unit 620, and a target size determining unit 630.

The target detection unit 610 may be configured to perform target detection on a medical image to determine a target object and a reference object in the medical image. The target object may be a tissue object that a user intends to observe in a medical image, for example, a cancer tissue, a polyp, anabrosis, erosion, edema, or another object. The reference object may be an object with a known reference size, for example, an instrument used during operating by using a medical electronic device, such as a scalpel, an electric scalpel, a suturing device, a pair of tweezers, or a pair of biopsy forceps. In some embodiments, in a medical image acquired during an intestinal examination by using an endoscope, a target image may be an image of a polyp, and a reference image may be an image of a pair of biopsy forceps. It may be understood that, during acquiring by using other types of medical electronic devices, the target object and the reference object involved in the present disclosure may be any other objects.

In some embodiments, the target detection may be performed by processing the medical image by using a neural network. For example, the medical image may be processed by using networks such as an RCNN, a fast RCNN, a faster RCNN, a YOLO, an SSD, a Mask RCNN, a deepLab, and other series, to recognize a target object and a reference object in the medical image.

By using the Mask RCNN network architecture shown in FIG. 3 to FIG. 5, a medical image may be processed, and a target mask of a target object and a reference mask of a reference object in the medical image may be determined. The target mask indicates a position of the target object and a boundary of the target object, and the reference mask indicates a position of the reference object and a boundary of the reference object.

In some embodiments, the target mask and the reference mask may be a binary image composed of 0 and 1, and a region of value 1 may correspond to a target object and a reference object detected in an input image. It may be understood that, the position and boundary of the target object and the position and boundary of the reference object can be determined by using a position and boundary of the region of value 1.

It may be understood that, because the reference object is a non-biological tissue such as a scalpel, an electric scalpel, a suturing device, a pair of tweezers, and a pair of biopsy forceps, and therefore, these reference objects usually have known shapes and sizes. Because the position and boundary of the target object and the position and boundary of the reference object can be segmented from the input image separately by using the method shown in FIG. 3, a size of the target object may be determined by using the shapes and sizes of the known reference object.

The feature size determining unit 620 may be configured to determine a feature size of the target object based on the target mask. In some embodiments, the feature size of the target object may include a plurality of feature sizes. For example, the plurality of feature sizes may include a distance between two most distant points in the target object, and distances between the two most distant points and a center point of the medical image.

For example, the feature size determining unit 620 may be configured to determine two target feature points in the target mask, a distance between the two target feature points indicating a maximum size of the target mask. The distance between the two target feature points may be determined as a first feature size of the target object.

Further, the feature size determining unit 620 may be further configured to: determine a distance between one target feature point in the two target feature points and a center of the medical image as a second feature size of the target object; and determine a distance between the other target feature point in the two target feature points and the center of the medical image as a third feature size of the target object.

Correspondingly, the feature size determining unit 620 may be configured to determine a feature size of the reference object based on the reference mask. In some embodiments, the feature size of the reference object and the feature size of the target object are determined in the same manner.

In some embodiments, the feature size of the reference object may include a plurality of feature sizes. The plurality of feature sizes may include a distance between two most distant points in the reference object, and distances between the two most distant points and a center point of the medical image.

For example, the feature size determining unit 620 may be configured to: determine two reference feature points in the reference mask, a distance between the two reference feature points indicating a maximum size of the reference mask; and determine the distance between the two reference feature points as a first feature size of the reference object.

Further, the feature size determining unit 620 may be further configured to: determine a distance between one reference feature point in the two reference feature points and a center of the medical image as a second feature size of the reference object; and determine a distance between the other reference feature point in the two reference feature points and the center of the medical image as a third feature size of the reference object.

The target size determining unit 630 may be configured to determine a target size of the target object based on the feature size of the reference object, the feature size of the target object, and the reference size, the reference size and the feature size of the reference object having a predefined mapping relationship.

In some embodiments, the target size determining unit 630 may be configured to determine at least one mapping parameter used in the mapping relationship based on the reference size and the feature size of the reference object. In some embodiments, the at least one mapping parameter is determined by using the following steps: fitting the feature size of the reference mask determined by using at least one medical image, to determine the at least one mapping parameter.

In some embodiments, the mapping relationship may be represented as that: the reference size can be represented as a function f of the feature size of the reference object.

In some embodiments, f may be represented in a form of a polynomial. The polynomial includes at least one variable, the at least one variable represents the feature size, and the mapping parameter is a coefficient of each term in the polynomial.

In some other implementations, the foregoing mapping relationship f may alternatively be represented as a functional expression of any another form. For example, the mapping relationship f may be represented by using a power function, an exponential function, a trigonometric function, and a function of any another form, and correspondingly, at least one mapping parameter in the mapping relationship may be determined.

A feature size of the target size may be processed by using the determined mapping parameter based on the mapping relationship, to determine the target size of the target object.

That is, after determining a value of the mapping parameter in the formula (2) by using the foregoing method, the target size of the target object may be determined by using the formula (4).

In some embodiments, for any medical image, a target size of a target object in the medical image may be determined based on a medical image set, including a plurality of medical images, of the medical image. For example, the target size of the target object may be determined based on an average value of candidate target sizes of the target object determined by using the plurality of medical images. In some other implementations, the target size of the target object may alternatively be determined by using a weighted average of the candidate target sizes of the target object determined by using a plurality of medical images.

In some embodiments, the medical image processing apparatus 600 may further include a judgment unit (not shown), and the judgment unit may be configured to: obtain a frame of image from a real-time medical video stream as the medical image; and determine whether the medical image meets a preset condition according to the target mask and the reference mask determined by the target detection unit 610. When the medical image meets the preset condition, a size of the target object in the medical image may be determined. When the medical image does not meet the preset condition, a size of the target object may not be determined based on the medical image, and another frame of image is obtained from the real-time medical video stream as the medical image.

In some embodiments, the target mask and the reference mask need to meet the following conditions:

There is a target object (for example, a polyp) of a predefined type and a reference object (for example, a head of a pair of biopsy forceps) of a predefined type in a medical image.

The target mask and the reference mask are not overlapped.

A distance between the target mask and a boundary of the medical image and a distance between the reference mask and the boundary of the medical image are greater than a preset first threshold (for example, 20 pixels).

A distance between a center point of the target mask and a center point of the medical image and a distance between a center point of the reference mask and the center point of the medical image are less than a preset second threshold (for example, 50 pixels).

When the target mask and the reference mask determined in the medical image meet the foregoing conditions, it may be considered that the medical image meet a condition for determining the size of the target object, the medical image includes the complete target object and reference object, and the target object and the reference object are relatively close to the center of the image, and therefore, the deformation is relatively small.

It may be understood that, in specific applications, a person skilled in the art may adjust the foregoing conditions according to an actual situation. For example, specific values of the first threshold and second threshold may be set according to an actual situation. In addition, a person skilled in the art may alternatively select to delete at least one of the foregoing four conditions, or add a new condition according to an actual situation.

In some embodiments, the medical image is an endoscopic image, and the reference object is a medical instrument or a part of a medical instrument.

In some embodiments, the target size of the target object may be determined by using a weighted average of a plurality of target sizes of the target object determined by using a plurality of medical images.

Through the medical image processing apparatus provided in the present disclosure, a size of a target object in a medical image can be determined according to a result of target detection performed on the medical image, so as to make measuring a target in a medical image in real time possible. An actual size of the target object is determined by fitting a reference mask having a known reference size and an actual size in the image, and the method provided in the present disclosure has stronger robustness and effectively avoids a problem of inaccurate measurement caused by the deformation caused by the lens of the image acquisition unit.

The term unit (and other similar terms such as subunit, module, submodule, etc.) in this disclosure may refer to a software unit, a hardware unit, or a combination thereof. A software unit (e.g., computer program) may be developed using a computer programming language. A hardware unit may be implemented using processing circuitry and/or memory. Each unit can be implemented using one or more processors (or processors and memory). Likewise, a processor (or processors and memory) can be used to implement one or more units. Moreover, each unit can be part of an overall unit that includes the functionalities of the unit.

Figure 7:
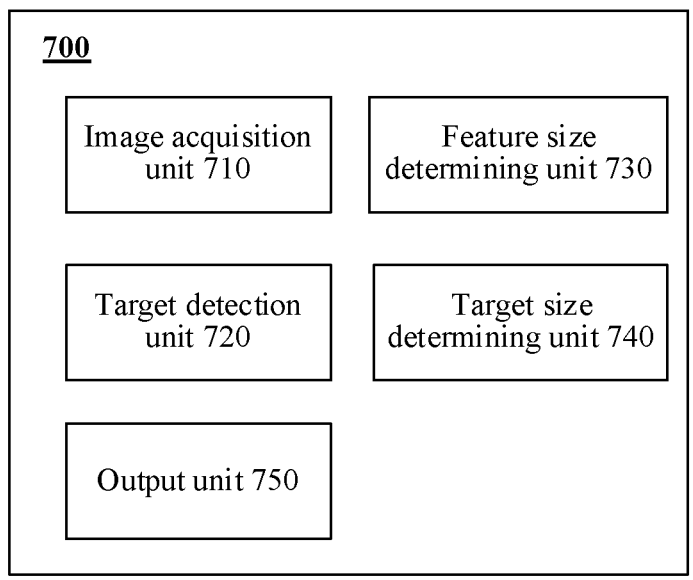
FIG. 7 is a schematic block diagram of a medical electronic device according to an embodiment of the present disclosure.

FIG. 7 is a schematic block diagram of a medical electronic device according to an embodiment of the present disclosure. As shown in FIG. 7, a medical electronic device 700 may include an image acquisition unit 710, a target detection unit 720, a feature size determining unit 730, and a target size determining unit 740.

The image acquisition unit 710 may be configured to acquire a medical image. The medical image may be a medical image acquired by using CT, MRI, ultrasound, X-ray, radionuclide imaging (such as SPECT and PET), optical imaging, and other methods, or may be an image displaying human physiological information by using an electrocardiogram, an electroencephalogram, optical photography, and the like. In this embodiment of the present disclosure, the medical electronic device 700 may be an endoscope. The image acquisition unit may be an image acquisition module located at a front end of the endoscope, including CCD or CMOS and optical components used for imaging.

In some embodiments, the image acquisition unit 710 may be configured to acquire a video stream including at least two medical images.

The target detection unit 720, the feature size determining unit 730, and the target size determining unit 740 may be implemented as the target detection unit 610, the feature size determining unit 620, and the target size determining unit 630 shown in FIG. 6, and details are not described herein again.

In some embodiments, a processing unit (for example, a processor) in the medical electronic device may be used to implement functions of the target detection unit 720, the feature size determining unit 730, and the target size determining unit 740. The processing unit may be configured to determine the target size of the target object in real time based on the at least two medical images.

The medical electronic device 700 may further include an output unit 750. The output unit 750 may be configured to output the determined target size of the target object.

For example, the output unit 750 may output the determined target size of the target object by sight or sound or in any other manners. For example, the output unit may display a target size of a target object in a currently displayed medical image at a display in real time, so as to provide a user with information of the target size in real time, further to help the user make decisions on a next operation.

Figure 8:
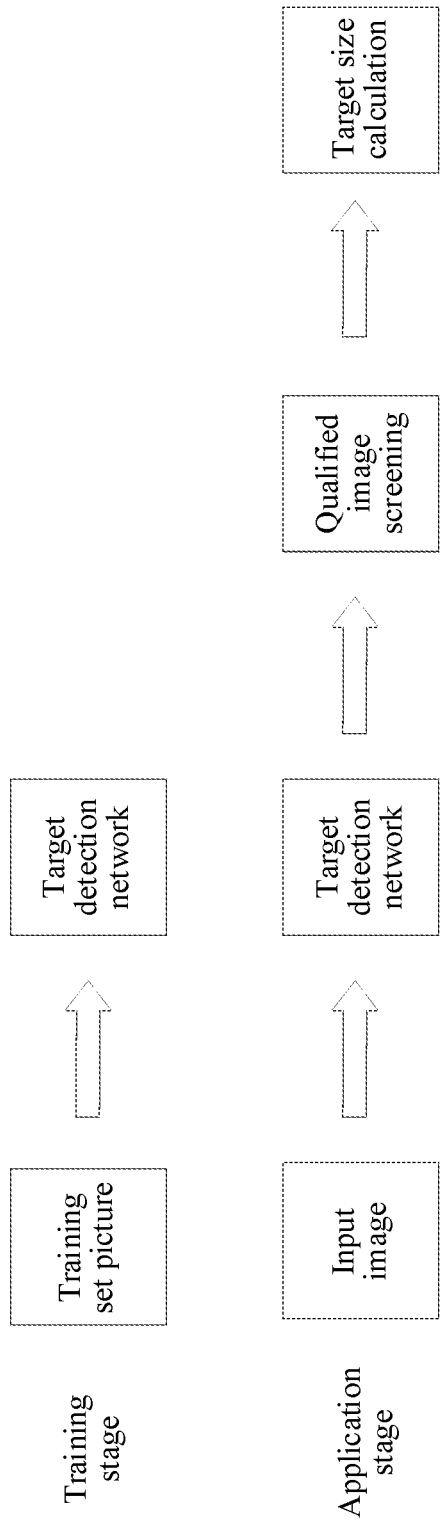
FIG. 8 shows a schematic process of an application process of a medical electronic device according to an embodiment of the present disclosure.

FIG. 8 shows a schematic process of an application process of a medical electronic device according to an embodiment of the present disclosure.

As shown in FIG. 8, at a training stage, a target detection network (for example, the foregoing Mask RCNN network) may be trained by using a predetermined training set picture, to determine a parameter in the target detection network.

At an application stage, input images (photographed pictures or video frames in an acquired video stream) acquired by the medical electronic device may be processed by using the trained target detection network. An image meeting a condition may be screened by screening images to be processed, and the image meeting a condition may be processed by using the method described in FIG. 2 to FIG. 5, to determine a target size of a target object in the image.

Figure 9:
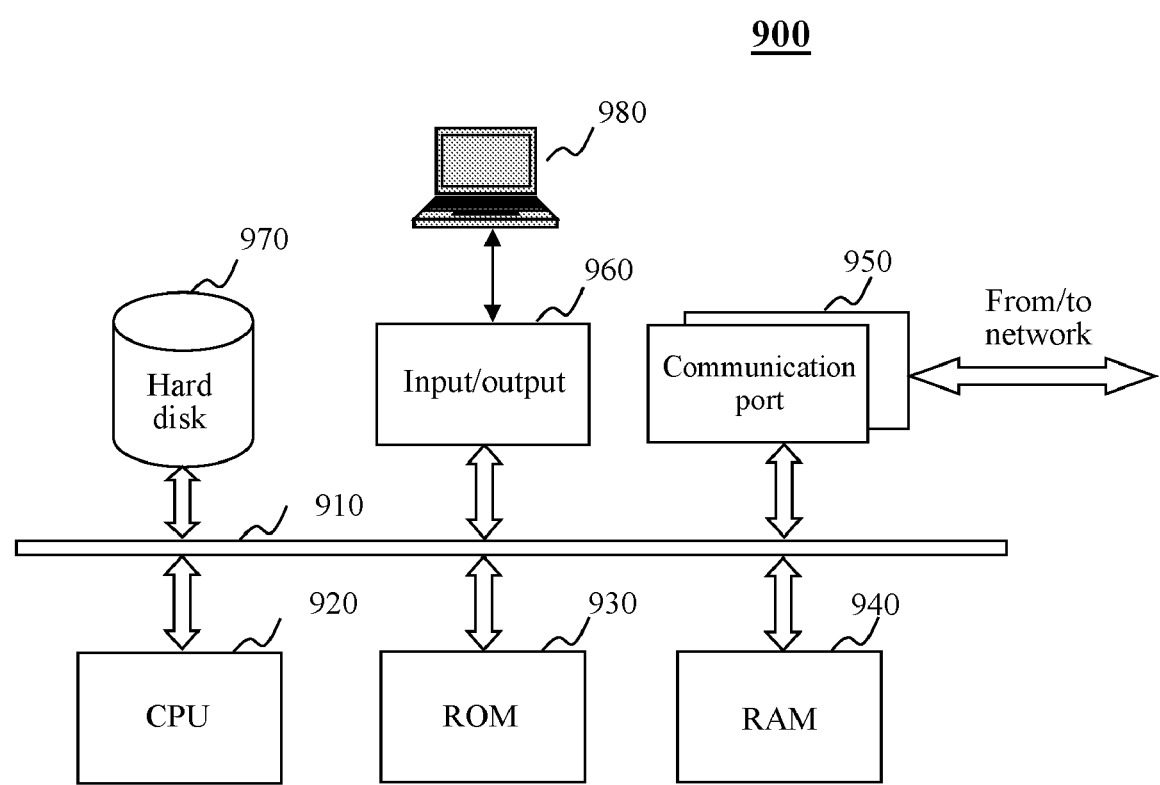
FIG. 9 shows an architecture of a computing device according to an embodiment of the present disclosure.

In addition, the method or apparatus according to the embodiments of the present disclosure may alternatively be implemented by using an architecture of a computing device shown in FIG. 9. FIG. 9 shows the architecture of the computing device. As shown in FIG. 9, a computing device 900 may include a bus 910, one or at least two CPUs 920, a ROM 930, a RAM 940, a communication port 950 connected to the network, an input/output component 960, a hard disk 970, or the like. A storage device in the computing device 900, for example, the ROM 930 or the hard disk 970 may store various data or files used in processing and/or communication of the target detection method provided in the present disclosure and program instructions performed by the CPU. The computing device 900 may further include a user interface (UI) 980. Certainly, the architecture shown in FIG. 9 is merely an example, and when implementing different devices, one or at least two components in the computing device shown in FIG. 9 may be omitted according to an actual requirement.

According to another aspect of the present disclosure, a non-volatile computer-readable storage medium is provided, storing a computer-readable instruction, being capable of performing the foregoing method when using a computer to perform the instruction.

A program part of a technology may be considered a "product" in the form of executable code and/or associated data that is engaged in or implemented through a computer-readable medium. Tangible and permanent storage media may include an internal memory or a memory used by any computer, processor, or similar device, or related module, for example, various semiconductor memories, tape drives, disk drives, or anything like that that can provide a storage function for software.

All software or a part of the software may sometimes communicate through a network, such as the Internet or other communication networks. Such communication may load software from one computer device or processor to another, for example, loading from a server or a host computer of a video target detection device to a hardware of a computer environment, or a computer environment of another implementation system, or a system with similar functions related to providing information required for target detection. Therefore, another medium that can transmit software elements can also be used as a physical connection between local devices, such as light waves, electric waves, and electromagnetic waves. The communication is implemented by using cables, optical cables, air, or the like. Physical media used for carrier waves, such as cables, wireless connections, optical cables, or other similar devices, can also be considered as the media for carrying software. Unless the use here limits the physical storage medium, other terms for computer or machine-readable media refer to the medium that is involved in the execution of any instruction by the processor.

The present disclosure uses specific words to describe the embodiments of the present disclosure. For example, the "first/second embodiment", "an embodiment" and/or "some embodiments' means a certain feature, structure, or characteristic related to at least one embodiment of the present disclosure. It should therefore be emphasized and noted that "an embodiment" or "an alternative embodiment" mentioned twice or more in different locations in this specification does not necessarily refer to the same embodiment. In addition, certain features, structures, or characteristics in one or more embodiments of the present disclosure may be appropriately combined.

In addition, it is understood by a person skilled in the art that aspects of the present disclosure may be illustrated and described by means of a plurality of categories or situations which are patentable, including any new and useful combination of processes, machines, products, or substances, or any new and useful improvement to them. Correspondingly, various aspects of the present disclosure may be entirely executed by hardware, may be entirely executed by software (including firmware, resident software, microcode, and the like), or may be executed by a combination of hardware and software. The foregoing hardware or software may be referred to as "data block", "module", "engine", "unit", "component" or "system". In addition, various aspects of the present disclosure may be embodied as computer products located in one or more computer-readable media, the product including a computer-readable program code.

Unless otherwise defined, all terms (including technical and scientific terms) used herein have the same meaning as commonly understood by a person of ordinary skill in the art to which the present disclosure belongs. It is further to be understood that, the terms such as those defined in commonly used dictionaries are to be interpreted as having meanings that are consistent with the meanings in the context of the related art, and are not to be interpreted in an idealized or extremely formalized sense, unless expressively so defined herein.

The above is description of the present disclosure, and is not to be considered as a limitation to the present disclosure. Although several exemplary embodiments of the present disclosure are described, a person skilled in the art may easily understand that, many changes can be made to the exemplary embodiments without departing from novel teaching and advantages of the present disclosure. Therefore, the changes are intended to be included within the scope of the present disclosure as defined by the claims. It is to be understood that, the above is description of the present disclosure, and is not to be considered to be limited by the disclosed specific embodiments, and modifications to the disclosed embodiments and other embodiments fall within the scope of the appended claims. The present disclosure is subject to the claims and equivalents thereof.

What is claimed is:

1. A medical image processing method, performed by one or more computing devices, the method comprising:
    determining a target mask of a target object in a medical image and a reference mask of a reference object in the medical image, the target mask indicating a position and a boundary of the target object, and the reference mask indicating a position and a boundary of the reference object, wherein the reference object is a non-tissue object with a known reference size;
    determining a feature size of the target object in the medical image based on the target mask;
    determining a feature size of the reference object in the medical image based on the reference mask; and
    determining a target size of the target object based on the feature size of the reference object, a mapping relationship between the feature size of the reference object and the known reference size of the reference object, and the feature size of the target object.

2. The method according to claim 1, further comprising:
    determining, according to the medical image, a type of the target object and the target mask of the target object, and a type of the reference object and the reference mask of the reference object in the medical image.

3. The method according to claim 1, wherein the determining a feature size of the target object based on the target mask comprises:
    determining two target feature points in the target mask, a distance between the two target feature points indicating a maximum size of the target object;
    determining the distance between the two target feature points as a first feature size of the target mask;
    determining a distance between one target feature point in the two target feature points and a center of the medical image as a second feature size of the target object; and
    determining a distance between the other target feature point in the two target feature points and the center of the medical image as a third feature size of the target object.

4. The method according to claim 1, wherein the determining a target size of the target object comprises:
    determining at least one mapping parameter used in the mapping relationship based on the known reference size and the feature size of the reference object; and
    determining the target size of the target object according to the feature size of the target object, and the at least one mapping parameter used in the mapping relationship.

5. The method according to claim 4, wherein determining the at least one mapping parameter comprises:
    fitting the feature size of the reference mask determined by using at least one related medical image, to determine the at least one mapping parameter.

6. The method according to claim 1, wherein the determining a feature size of the reference object based on the reference mask comprises:
    determining two reference feature points in the reference mask, a distance between the two reference feature points indicating a maximum size of the reference mask;
    determining the distance between the two reference feature points as a first feature size of the reference object;
    determining a distance between one reference feature point in the two reference feature points and a center of the medical image as a second feature size of the reference object; and
    determining a distance between the other reference feature point in the two reference feature points and the center of the medical image as a third feature size of the reference object.

7. The method according to claim 4, wherein the mapping relationship is represented in a form of a polynomial, the polynomial comprises at least one variable, the at least one variable represents the feature size of the reference object, and the mapping parameter is a coefficient of each term in the polynomial.

8. The method according to claim 1, further comprising:
    obtaining a frame of image from a real-time medical video stream as the medical image;

determining whether the medical image meets a preset condition according to the target mask and the reference mask;

determining the target size of the target object based on the feature size of the reference object, the feature size of the target object, and the reference size when the medical image meets the preset condition; and obtaining another frame of image from the real-time medical video stream as the medical image when the medical image does not meet the preset condition.

9. The method according to claim 1, wherein the medical image is an endoscopic image, and the reference object is a medical instrument or a part of a medical instrument.

10. The method according to claim 1, wherein the determining a target size of the target object comprises:

determining the target size of the target object by using a weighted average of a plurality of target sizes of the target object determined by using a plurality of medical images.

11. A medical image processing apparatus, comprising: one or more processors; and one or more memories, the memory storing computer-readable code, wherein the one or more processors are configured to execute the computer-readable code to:

determine a target mask of a target object in a medical image and a reference mask of a reference object in the medical image, the target mask indicating a position and a boundary of the target object, and the reference mask indicating a position and a boundary of the reference object, wherein the reference object is a non-tissue object with a known reference size;

determine a feature size of the target object in the medical image based on the target mask;

determine a feature size of the reference object in the medical image based on the reference mask; and determine a target size of the target object based on the feature size of the reference object, a mapping relationship between the feature size of the reference object and the known reference size of the reference object, and the feature size of the target object.

12. The apparatus according to claim 11, wherein the one or more processors are further configured to: determine, according to the medical image, a type of the target object and the target mask of the target object, and a type of the reference object and the reference mask of the reference object in the medical image.

13. The apparatus according to claim 11, wherein the one or more processors are further configured to:

determine two target feature points in the target mask, a distance between the two target feature points indicating a maximum size of the target mask;

determine the distance between the two target feature points as a first feature size of the target object;

determine a distance between one target feature point in the two target feature points and a center of the medical image as a second feature size of the target object; and determine a distance between the other target feature point in the two target feature points and the center of the medical image as a third feature size of the target object.

14. The apparatus according to claim 11, wherein the one or more processors are further configured to:

determine at least one mapping parameter used in the mapping relationship based on the known reference size and the feature size of the reference object; and determine the target size of the target object according to the feature size of the target object, and the at least one mapping parameter used in the mapping relationship.

15. The apparatus according to claim 14, wherein the one or more processors are further configured to fit the feature size of the reference mask determined by using at least one related medical image, to determine the at least one mapping parameter.

16. The apparatus according to claim 14, wherein the one or more processors are further configured to:

determine two reference feature points in the reference mask, a distance between the two reference feature points indicating a maximum size of the reference mask;

determine the distance between the two reference feature points as a first feature size of the reference object;

determine a distance between one reference feature point in the two reference feature points and a center of the medical image as a second feature size of the reference object; and determine a distance between the other reference feature point in the two reference feature points and the center of the medical image as a third feature size of the reference object.

17. The apparatus according to claim 11, wherein the one or more processors are further configured to:

obtain a frame of image from a real-time medical video stream as the medical image;

determine whether the medical image meets a preset condition according to the target mask and the reference mask;

determine the target size of the target object based on the feature size of the reference object, the feature size of the target object, and the reference size when the medical image meets the preset condition; and obtain another frame of image from the real-time medical video stream as the medical image when the medical image does not meet the preset condition.

18. The apparatus according to claim 11, wherein the medical image is an endoscopic image, and the reference object is a medical instrument or a part of a medical instrument.

19. The apparatus according to claim 11, wherein the one or more processors are further configured to:

determine the target size of the target object by using a weighted average of a plurality of target sizes of the target object determined by using a plurality of medical images.

20. A non-transitory computer-readable storage medium, storing instructions, the instructions, when executed by a processor, causing the processor to perform:

determining a target mask of a target object in a medical image and a reference mask of a reference object in the medical image, the target mask indicating a position and a boundary of the target object, and the reference mask indicating a position and a boundary of the reference object, wherein the reference object is a non-tissue object with a known reference size;

determining a feature size of the target object in the medical image based on the target mask;

determining a feature size of the reference object in the medical image based on the reference mask;

determining at least one mapping parameter used in a mapping relationship between the feature size of the reference object and the known reference size of the reference object based on the known reference size and the feature size of the reference object; and determining a target size of the target object based on the feature size of the reference object, the at least one mapping parameter used in the mapping relationship between the feature size of the reference object and the known reference size of the reference object, and the feature size of the target object.

* * * * *